US006979196B2

(12) United States Patent
Nikolskiy et al.

(10) Patent No.: US 6,979,196 B2
(45) Date of Patent: Dec. 27, 2005

(54) SYSTEMS AND METHODS FOR AUTOMATED BITE-SETTING OF TOOTH MODELS

(75) Inventors: Sergey Nikolskiy, Moscow (RU); Huafeng Wen, Redwood Shores, CA (US)

(73) Assignee: Align Technology, Inc., Santa Clara, CA (US)

( * ) Notice: Subject to any disclaimer, the term of this patent is extended or adjusted under 35 U.S.C. 154(b) by 396 days.

(21) Appl. No.: 10/176,805

(22) Filed: Jun. 21, 2002

(65) Prior Publication Data

US 2003/0235803 A1    Dec. 25, 2003

(51) Int. Cl.⁷ .................................................. A61C 9/00
(52) U.S. Cl. ...................................................... 433/214
(58) Field of Search ........................... 433/24, 213, 214

(56) References Cited

U.S. PATENT DOCUMENTS

| | | |
|---|---|---|
| 2,467,432 A | 4/1949 | Kesling |
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |

(Continued)

FOREIGN PATENT DOCUMENTS

EP           0091876 A1      10/1983

(Continued)

OTHER PUBLICATIONS

Andrews, "The Six Keys to Optimal Occlusion" Straight Wire, Chapter 3 pp 13-24.

(Continued)

*Primary Examiner*—Cary E. O'Connor
(74) *Attorney, Agent, or Firm*—Align Technology, Inc.; Greenberg Traurig, LLP

(57) ABSTRACT

A method to bite set a dental model includes: scanning upper and lower arches of the dental model; scanning the upper and lower arches in their bite position; and aligning the upper and lower arches.

16 Claims, 8 Drawing Sheets

U.S. PATENT DOCUMENTS

| | | |
|---|---|---|
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,367,478 A | 11/1994 | Hattori |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Anderson et al. |
| 5,605,459 A | 2/1997 | Kuroda et al. |
| 5,607,305 A | 3/1997 | Andersson et al. |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,800,174 A | 9/1998 | Andersson |
| 5,866,058 A | 2/1999 | Batchelder et al. |
| 5,879,158 A | 3/1999 | Doyle et al. |
| 5,880,961 A | 3/1999 | Crump |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chisti et al. |
| 6,044,309 A | 3/2000 | Honda |
| 6,049,743 A | 4/2000 | Baba |
| 6,123,544 A | 9/2000 | Cleary |
| 6,152,731 A * | 11/2000 | Jordan et al. ............ 433/69 |
| 6,183,248 B1 | 2/2001 | Chisti et al. |
| 6,190,165 B1 | 2/2001 | Andreiko et al. |
| 6,217,334 B1 | 4/2001 | Hultgren |
| 6,726,478 B1 | 4/2004 | Isiderio et al. |
| 2002/0025503 A1* | 2/2002 | Chapoulaud et al. ........ 433/24 |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2369828 | 6/1978 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 | 5/1994 |
| WO | WO 94/10935 A1 | 5/1994 |
| WO | WO 98/32394 | 7/1998 |
| WO | WO 98/58596 | 7/1998 |
| WO | WO 98/44865 A1 | 10/1998 |
| WO | WO 98/58596 A1 | 12/1998 |

OTHER PUBLICATIONS

Biostar Operation & Training Manual. Great Lakes Othodontics, Ltd. 199 Fire Tower Drive, Tonawanda, New York. 14150-5890. 20 pages total.

Chiappone, "Constructing the gnathologic setup and positioner" J. Clin. Othod. (1980) 14:121-133.

Cottingham, "Gnathologic clear the plastic positioner" Am. J. Orthod. (1969) 55:23-31.

Cureton, "Correcting malaligned mandibular incisors with removable retainers" J. Clin. Orthod. (1996) 30:390-395.

Dent-X posted at http://www.dent-x.com/DentSim.htm Sep. 24, 1998. 6 pages total.

Elasser, "Some observations on the history and uses of the Kesling positioner" Am. J. Orthod. (1950) 36:368-374.

Kamada et al., "Case reports on tooth positioners using LTV vinyl silicone rubber" *J. Nihon University School of Dentistry* (1984) 26(1):11-29.

Kamada et al., "Construction of tooth positioners with LTV vinyl silicone rubber and some case reports" *J. Nihon University of School of Dentistry (1982) 24(1):1-27*.

Kesling, "Coordinating the predetermined pattern and tooth positioner with conventional treatment" Am J. Orthod. Oral Surg. (1946) 32:285-293.

Kesling, "The philosophy of the tooth positioning appliance" Am. J. Orthod. Oral. Surg. (1945) 32 (6):297-304.

Kleemann et al., "The speed positioner" J. Clin. Orthod. (1996) 30:673-680.

Kunii et al., "Articulation Simulation for an Intelligent Dental Care System" Displays (1994) 15:181-188.

Kuroda et al., "Three-dimensional dental cast analyzing system using laser scanning" Am J. Orthod. Dentofac. Orthop. (1996) 110:365-369.

Nahoum et al., "The vacuum formed dental contour appliance" *The New York State Dental Journal (1964) 30(9):385-390*.

Nippon Dental Review "New orthodontic device-dynamic positioner (D.P.)-I. Approach to the proposal of D.P. and transparent silicone rubber" (1980) 452:61-74.

Nippon Dental Review "New orthodontic device-dynamic positioner (D.P.)-II. Practical application and construction of D.P." (1980) 454:107-130.

*Nippon Dental Review* "New Orthodontic device-dynamic positioner (D.P.)-III. Case reports of reversed occlusion" (1980) 457:146-164.

*Nippon Dental Review* "New orthodontic device-dynamic positioner (D.P.)-Case reports of reversed occlusion" (1980) 458:112-129.

Nishiyama et al., "A new construction of tooth repositioner by LTV vinyl silicone rubber" *J. Nihon University School of Dentistry* (1977) 19(2):93-102.

Cardinal Industrial Finishes, Powder Coatings information posted at http://www.cardinalpaint.com on Aug. 25, 2000, 2 pages total.

Proffit et al, "Contemporary Orthodontics" Second Edition, Chapter 15, pp 470-533.

*Raintree Essix™ & ARS Materials, Inc., Raintree Essix*198 Technical Magazine Table of Contents and Essix™ Applications http://www.essix.com/magazine.default.html (Aug. 13, 1997) 7 pages total.

Richmond et al., "The development of the PAR Index (Peer Assessment Rating): reliability and validity" *European Journal of Orthodontics* (1992) 14:125-139.

Schroeder et al., Eds. *The Visual Toolkit*, Prentice Hall PTR, New Jersey (1998) Chapters 6, 8, and 9 (pp. 153-210, 309-354, and 355-428, respectively).

Shilliday, "Minimizing finishing problems with the minipositioner" *Am. J. Orthod.* (1971) 59:596-599.

Warunkek at el., "Clinical use of silicone elastomer appliances" JCO (1989) XXIII(10):694-700.

Warunek et al., "Physical and mechanical properties of elastomers in orthodontic positioners" *Am. J. Orthod. Dentofac. Orthop.* (1989) 95:388-400.

Wells, "Application of the positioner appliance in orthodontic treatment"*Am. J. Orhhdont.* (1970) 58:351-366.

Doyle, "Digital Dentistry" Computer Graphics World (Oct. 2000) pp. 50-52, 54.

Redmond et al., "Clinical Implications of Digital Orthodontics" Am. J. Orthodont. Dentofacial Orthopedics (2000) 117(2):240-242.

Alexander et al., "The DigiGraph Work Station Part 2, Clinical Management," *JCO* (Jul. 1990), pp. 402-407.

Altschuler et al, ,"Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures, " IADR Abstracts, Program and Abstracts of Papers, 57th General Session, IADR Annual Session, Mar. 29, 1979—Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607, 1980, 1 page total..

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars In Orthodontics*, vol. 7, No. 4 (Dec. 2000), pp. 223-232.

Begole et al., "A Computer System for the Analysis of Dental Casts," *The Angle Orthodontist*, vol. 51, No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion in the Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7, Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, vol. 55, No. 1 ( Jan. 1969), pp. 23-31.

Crawford, "Computers in Dentistry: Part 1: CAD/CAM: The Computer Moves Chairside," "Part 2: F. Duret—A Man With A Vision," "Part 3: The Computer Gives New Vision-Literally," "Part 4: Bytes 'N Bites" The Computer Moves From The Front Desk To The Operatory, *Canadian Dental Journal*, vol. 54(9) . . . (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al, "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May 1950) pp. 368-374.

Faber et al.,"Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery, "Abstract of Papers, *Journal of Dental Research*, vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery, "*JCO*, (Apr. 1989), pp. 262-28.

Heaven et al., "Computer-based Image Analysis of Artificial Root Surface Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko, DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.*, vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

Manetti et al., "Computer-aided Cefalometry and New Mechanics in Orthodontics" ( Article Summary in English, article in German), *Fortschr. Kieferorthop.* 44, 370-376 (Nr. 5), 1983.

McCann, Inside the ADA, *Journal Of The American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro, "Schwizerische Monatsshrift fur Zahnmedizin, vol. 85 (1985), p. 1118-1129.

Nahoum, "The Vacuum Formed Dental Contour Appliance" The New York State Dental Journal, 30(9):385-390, Nov. 1964.

Nash, "CERAC CAD/CAM Inlays: Aesthetics and Durability in a Single Appointment," Dentistry Today, (Oct. 1990), pp. 20, 22-23, 54.

Nishiyama et al.,"A New Construction Of Tooth Repositioner By LTV Vinyl Silicone Rubber" J. Nihon University School of Dentistry, 19(2):93-102, 1977.

Pinkham, "'Foolish' Concept Propels Technology," Dentist, Jan./Feb. 1989, 3 pages total.

Pinkham, "Inventor's CAD/CAM May Transform Dentistry," Dentist, Sep. 1990, 3 pages total.

Ponitz," Invisible Retainers", Am. J. Orthodontics, vol. 59, No. 3, Mar. 1971, pp. 266-272.

Procera Research Projects, PROCERA Research Projects 1993—Abstract Collection, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: Prosthodontics and Endodontics, pp. 25-33, 1992.

Rekow, "CAD/CAM in Dentistry: A Historical Perspective and View of the Future," Journal, vol. 58 No. 4, (Apr. 1992), pp. 283, 287-288.

Rekow, "Computer-Aided Design and Manufacturing in Dentistry: A Review of the State of the Art," The Journal of Prosthetic Dentistry, vol. 58, No. 4 (Oct. 1987), pp. 512-516.

Van Der Zel, "Ceramic-fused-to-metal Restorations with a New CAD/CAM System," Quintessence International, vol. 24(11) (1993), pp. 769-778.

Varady et al., Reverse Engineering Of Geometric Models—An Introduction. Computer-Aided Design, 29 (4): 255-268, 1997.

Warunek et al., "Clinical Use Of Silicone Elastomer Appliances" JCO, MH (10):694-700, 1989.

Warunek et al., "Physical And Mechanical Properties In Orthodontic Positioners" Am. J. Orthod. Dentofac. Orthop., 95:388-400, 1989.

Wells, "Application of the Positioner Appliance in Orthodontic Treatment" Am. J. Orthodont., 58:351-366, 1970.

Williams, "Dentistry and CAD/CAM: Another French Revolution, "Journal of Dental Practice Admin., Jan./Mar. 1987, pp. 2-5.

Williams, "The Switzerland and Minnesota Developments in CAD/CAM," Journal of Dental Practice Admin., pp. 50-55, Apr./Jun. 1987.

Wishan, "New Advances in Personal Computer Applications for Cephalometric Analysis, Growth Prediction, Surgical Treatment Planning and Imaging Processing, " Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, Journal of Oral and Maxillofacial Surgery, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," Frontiers In Med. and Biol. Eng'g, vol. 1, No. 2 (1988), pp. 119-130.

Rekow, "Dental CAD-CAM Sytems: What is the State of the Art?" Journal of the American Dental Assoc., vol. 122 (1991), pp. 43-48.

Rekow, Feasibility of an Automated System for Production of "Dental Restorations," PhD Thesis, Univ. of Minnesota, Nov. 1988, 244 pages total.

Richmond et al., Research Reports, "The Development of a 3D Cast Analysis System," British Journal of Orthodontics, vol. 13, No. 1, (Jan. 1986) pp. 53-54.

Richmond, "Recording The Dental Cast In Three Dimensions," Am. J. Orthod. Dentofac. Orthop., vol. 92, No. 3, (Sep. 1987), pp. 199-206.

Rudge, "Dental arch analysis: Arch Form, A review of the literature," European Journal of Orthodontics, vol. 3, No. 4 (1981), pp. 279-284.

Sakuda et al., "Integrated information-processing system in clinical orthodontics; An approach with use of a computer network system," Am. J. Orthod. Dentofac. Orthop. vol. 101 No. 3 (Mar. 1992), pp. 210-220.

Schellhas et al., "Three-Dimensional Computed Tomography in Maxillofacial Surgical Planning," Arch Otolamgol Head Neck Surg. vol. 114 (Apr. 1988), pp. 438-442.

Shilliday, "Minimizing Finishing Problems With the Mini-Positioner" Am. J. Orthod. 59:596-599, 1971.

Siemens, "CEREC—Computer-Reconstruction, "High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), Dtsch Zahnärztl Z 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed on Jun. 20, 1997, 41 pages total.

Van Der Linden et al., "Three-Dimensional Analysis of Dental Casts by Means of the Optocom," J Dent Res, Jul.-Aug. 1972, vol. 51, No. 4, p. 1101.

Van Der Linden, "A New Method to Determine Tooth Positions and Dental Arch Dimensions," Jul.-Aug. 1972, p. 1104.

* cited by examiner

300

┌─────────────────────────────────────────────────────┐
│ 302 Scan lower arch using the destructive scanner   │
│     or white light scanner                          │
└─────────────────────────────────────────────────────┘
                          ↓
┌─────────────────────────────────────────────────────┐
│ 304 Scan upper arch using the destructive scanner   │
│     or white light scanner                          │
└─────────────────────────────────────────────────────┘
                          ↓
┌─────────────────────────────────────────────────────┐
│ 306 Wax scan the upper and lower arches in their    │
│     bite position using white light scanner         │
└─────────────────────────────────────────────────────┘
                          ↓
┌─────────────────────────────────────────────────────┐
│ 308   Split apart the upper and lower arch scans    │
└─────────────────────────────────────────────────────┘
                          ↓
┌─────────────────────────────────────────────────────┐
│ 310   Register the bite using geometry matching     │
└─────────────────────────────────────────────────────┘

FIG. 4

┌─────────────────────────────────────────────────────┐
│ 322 Place wax bite between upper and lower arches   │
└─────────────────────────────────────────────────────┘
                          ↓
┌─────────────────────────────────────────────────────┐
│ 324 Align the upper and lower arches based on wax   │
│     bite to indicate their normal bite position     │
└─────────────────────────────────────────────────────┘
                          ↓
┌─────────────────────────────────────────────────────┐
│ 326              Remove wax bite                    │
└─────────────────────────────────────────────────────┘
                          ↓
┌─────────────────────────────────────────────────────┐
│ 328 Perform buccal scan of upper & lower arch in    │
│     normal bite position without wax bite           │
└─────────────────────────────────────────────────────┘

FIG. 5

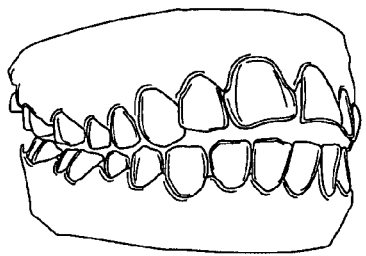
FIG. 8
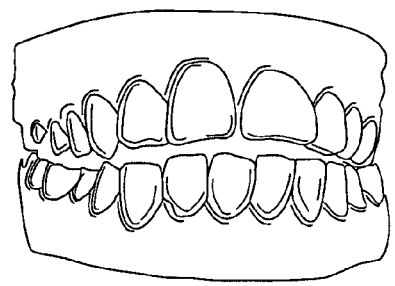
FIG. 9
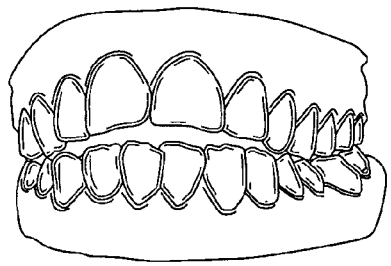
FIG. 10
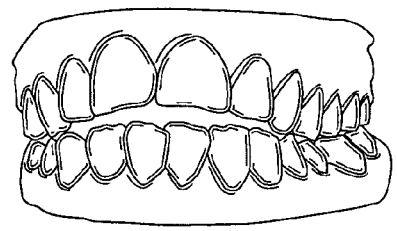
FIG. 11
| 350 | Move the upper jaw closer to the lower, for example, in the Z axis direction |
|---|---|
↓
| 352 | Compute collisions |
|---|---|
↓
| 354 | Minimize the collision areas using an appropriate algorithm. (See figures 8 and 9 for two possible implementations.) |
|---|---|
FIG. 12

360 Attempt to rotate or shift the upper jaw in all 5 degrees of freedom, with the Z direction excluded 362 Select the position in which the collision area or any other appropriate measure (for example, collision volume) is minimal 364 Minimize the collision areas using an appropriate algorithm

FIG. 13

370 Select the direction to move the jaw by using dental knowledge of the collision areas between the jaws 372 Using mechanical laws, one creates a system of differential equations, which are used to reduce the collision area 374 The process stops when it is impossible to move the upper jaw further down without introducing acceptable collision areas that cannot be achieved through translation and rotation

FIG. 14

SYSTEMS AND METHODS FOR AUTOMATED BITE-SETTING OF TOOTH MODELS

CROSS-REFERENCES TO RELATED APPLICATIONS

This application is related to U.S. patent application Ser. No. 09/702,360, filed on Oct. 30, 2000 now U.S. Pat. No 6,726,478, and entitled "Systems and Methods for Bite-Setting Teeth Models and related to U.S. patent application Ser. No. 09/169,276, filed on Oct. 8, 1998 now abandoned, and entitled "Computer Automated Development of an Orthodontic Treatment Plan and Appliance," which claims priority from PCT application PCT/US98/12681, filed on Jun. 19, 1998, and entitled "Method and System for Incrementally Moving Teeth", which claims priority from U.S. patent application Ser. No. 08/947,080, filed on Oct. 8, 1997, now U.S. Pat. No. 5,975,893, which claims priority from U.S. provisional application No. 60/050,342, filed on Jun. 20, 1997, all of which are incorporated by reference into this application.

BACKGROUND OF THE INVENTION

The present invention is related generally to the field of orthodontics, and more particularly to systems and methods for bite-setting teeth models.

One objective in orthodontics is to move a patient's tooth to a position where the tooth functions optimally and aesthetically. Conventionally, appliances such as braces are applied to the teeth of the patient by an orthodontist; each appliance exerts continual forces on the teeth and gradually urges the teeth toward their ideal positions. Over a period of time, the orthodontist adjusts the appliances to move the teeth toward their final destination.

Generally, the orthodontist specifies the final tooth arrangement in a prescription. The prescription is based on the orthodontist's knowledge and experience in selecting the intended final position of each tooth. The orthodontist or an assistant implements the prescription to move the teeth over a number of office visits.

The process of attaching the braces to teeth is tedious and painful to the patient. Additionally, each visit reduces "chair-time" available to the orthodontist that can be used for another patient.

New methods such as those described in U.S. Pat. No. 5,975,893, allow the treatment to be planned in advance and all individual appliances fabricated at the outset of treatment. The appliances may thus be provided to the patient as a single package or system. Unlike braces, the patient need not visit the treating professional every time an adjustment in the treatment is made. While the patients will usually want to visit their treating professionals periodically to assure that treatment is going according to the original plan, eliminating the need to visit the treating professional each time an adjustment is to be made allows the treatment to be carried out in many more, but smaller, successive steps while still reducing the time spent by the treating professional with the individual patient. Moreover, the ability to use polymeric shell appliances that are more comfortable, less visible, and removable by the patient, greatly improves patient compliance, comfort, and satisfaction.

In the above system, and in other computer-aided teeth treatment systems, as a first step, a digital data set representing an initial tooth arrangement is obtained, referred to hereinafter as the IDDS. The IDDS may be obtained in a variety of ways. For example, the patient's teeth may be scanned or imaged using well known technology, such as X-rays, three-dimensional x-rays, computer-aided tomographic images or data sets, magnetic resonance images, etc. Methods for digitizing such conventional images to produce data sets useful in the present invention are well known and described in the patent and medical literature. Usually, however, the present invention will rely on first obtaining a plaster cast of the patient's teeth by well known techniques, such as those described in Graber, Orthodontics: Principle and Practice, Second Edition, Saunders, Philadelphia, 1969, pp. 401–415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set, as described in more detail below. General techniques for producing plaster casts of teeth and generating digital models using laser-scanning techniques are described, for example, in U.S. Pat. No. 5,605,459. After scanning, computer models of teeth on an upper jaw and a lower jaw are generated. However, these models are not aligned relative to each other. Thus, a bite setting operation is manually performed using human operators.

SUMMARY

The present invention includes a system, apparatus and computer-implemented method for bite setting a dental model. This is done by scanning upper and lower arches of the dental model; scanning the upper and lower arches in their bite position; splitting the scan of the arches in their bite position into two jaw models; and registering the bite.

Implementations of the may include one or more of the following.

Advantages of the invention include one or more of the following. When digital data relating to teeth on the upper and lower jaws is provided, a bite-aligned computer model can be generated. By providing a visual picture of one jaw relative to another jaw, the system eliminates guesswork as to the bite setting for the models of the teeth on the jaws. The operation can be performed using little or no human labor.

BRIEF DESCRIPTION OF THE DRAWINGS

FIGS. 4–6 are flow charts illustrating a process for bite-setting two jaws.

FIGS. 8–11 are computer images of an exemplary bite registration process using a cast model of a patient's teeth.

FIGS. 12–14 are flow charts illustrating a process for creating a proper occlusion between the two jaws.

DESCRIPTION

Figure 1:
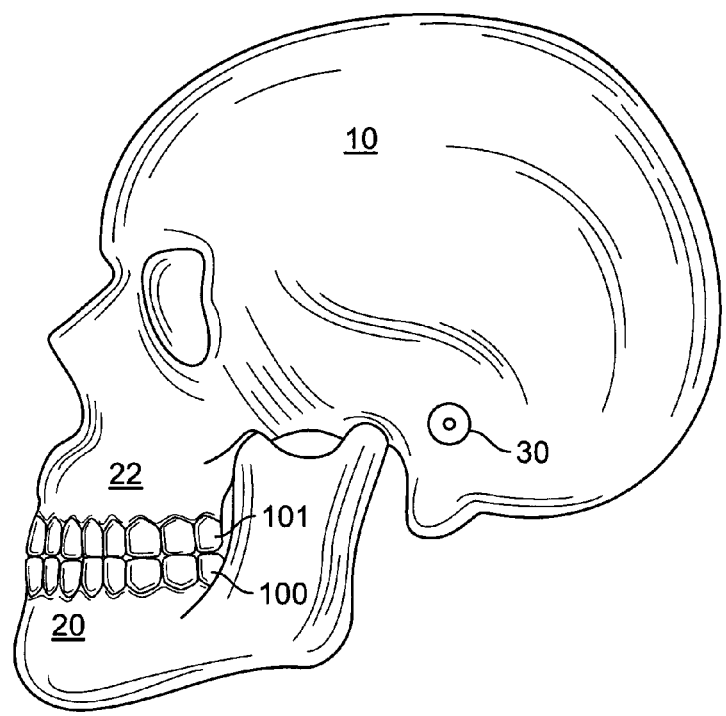
FIG. 1 is an elevational diagram showing the anatomical relationship of the jaws of a patient.

FIG. 1 shows a skull 10 with an upper jawbone 22 and a lower jawbone 20. The lower jawbone 20 hinges at a joint 30 to the skull 10. The joint 30 is called a temporal mandibular joint (TMJ). The upper jawbone 22 is associated with an upper jaw 101, while the lower jawbone 20 is associated with a lower jaw 100. A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements that are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
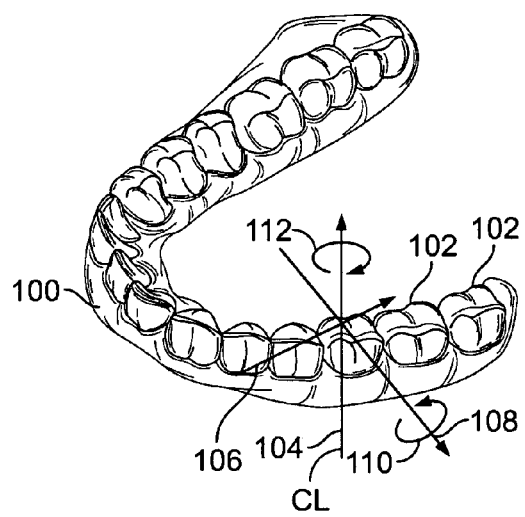
FIG. 2A illustrates in more detail the patient's lower jaw and provides a general indication of how teeth may be moved by the methods and apparatus of the present invention.

Referring now to FIG. 2A, the lower jaw 100 includes a plurality of teeth 102, for example. At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline. Thus, all possible free-form motions of the tooth can be performed.

Figure 2B:
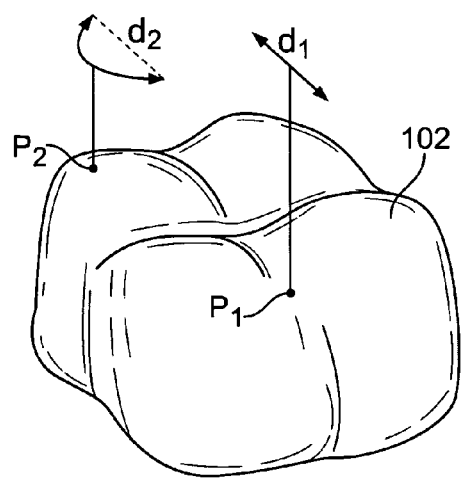
FIG. 2B illustrates a single tooth from FIG. 2A and defines how tooth movement distances are determined.

FIG. 2B shows how the magnitude of any tooth movement may be defined in terms of a maximum linear translation of any point P on a tooth 102. Each point $P_1$ will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point $P_1$ may in fact undergo a true side-to-side translation as indicated by arrow $d_1$, while a second arbitration point $P_2$ may travel along an accurate path, resulting in a final translation $d_2$. Many aspects of the present invention are defined in terms of the maximum permissible movement of a point $P_1$ induced on any particular tooth. Such maximum tooth movement, in turn, is defined as the maximum linear translation of that point $P_1$ on the tooth that undergoes the maximum movement for that tooth in any treatment step.

Figure 2C:
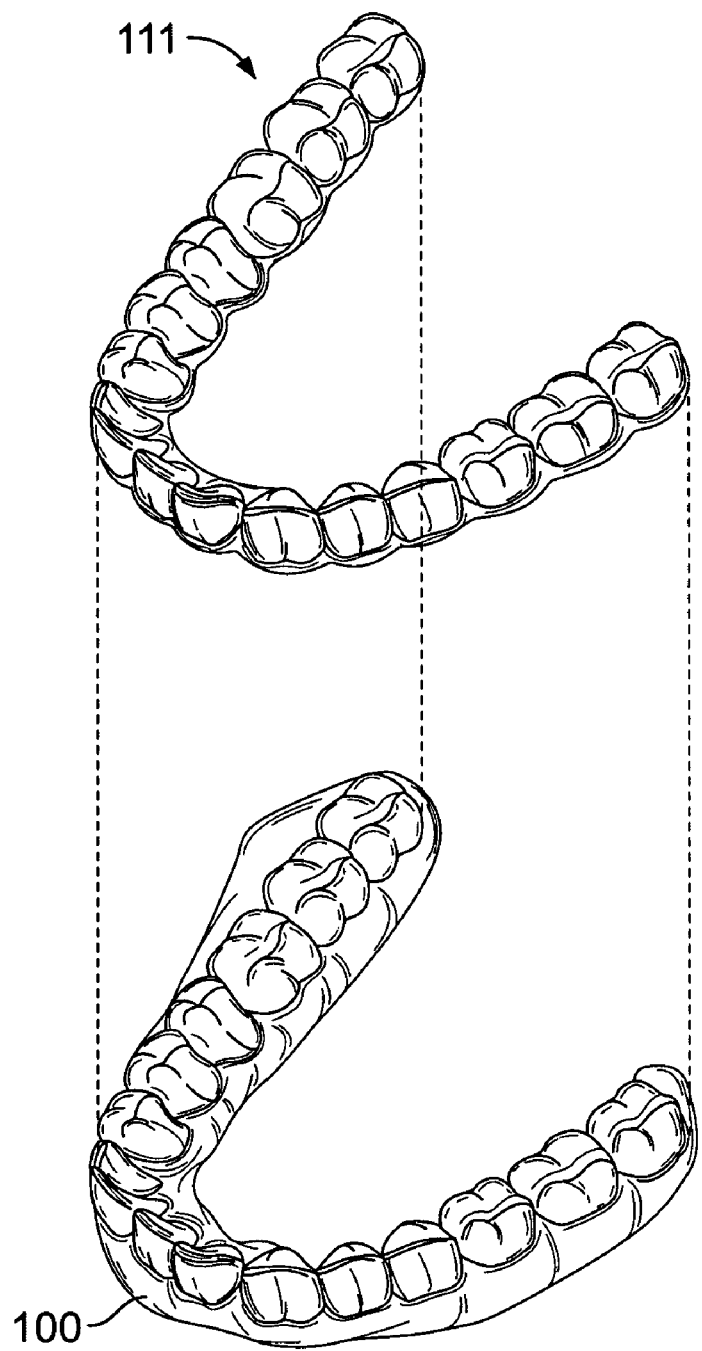
FIG. 2C illustrates the jaw of FIG. 2A together with an incremental position adjustment appliance.

FIG. 2C shows one adjustment appliance 111, which is worn by the patient in order to achieve an incremental repositioning of individual teeth in the jaw, as described generally above. The appliance is a polymeric shell having a teeth-receiving cavity. This is described in U.S. application Ser. No. 09/169,036, filed Oct. 8, 1998, which claims priority from U.S. application Ser. No. 08/947,080, filed Oct. 8, 1997, which in turn claims priority from provisional application No. 60/050,352, filed Jun. 20, 1997 (collectively the "prior applications"), the full disclosures of which are incorporated by reference.

As set forth in the prior applications, each polymeric shell may be configured so that its tooth-receiving cavity has a geometry corresponding to an intermediate or final tooth arrangement intended for the appliance. The patient's teeth are repositioned from their initial tooth arrangement to a final tooth arrangement by placing a series of incremental position adjustment appliances over the patient's teeth. The adjustment appliances are generated at the beginning of the treatment, and the patient wears each appliance until the pressure of each appliance on the teeth can no longer be felt. At that point, the patient replaces the current adjustment appliance with the next adjustment appliance in the series until no more appliances remain. Conveniently, the appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

The polymeric shell 111 can fit over all teeth present in the upper or lower jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the moved teeth can also serve as a base or anchor region for holding the repositioning appliance.

The polymeric appliance 111 of FIG. 2C may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth. In some cases, however, it will be desirable or necessary to provide individual anchors on teeth with corresponding receptacles or apertures in the appliance 111 so that the appliance can apply an upward force on the tooth that would not be possible in the absence of such an anchor.

Figure 3:
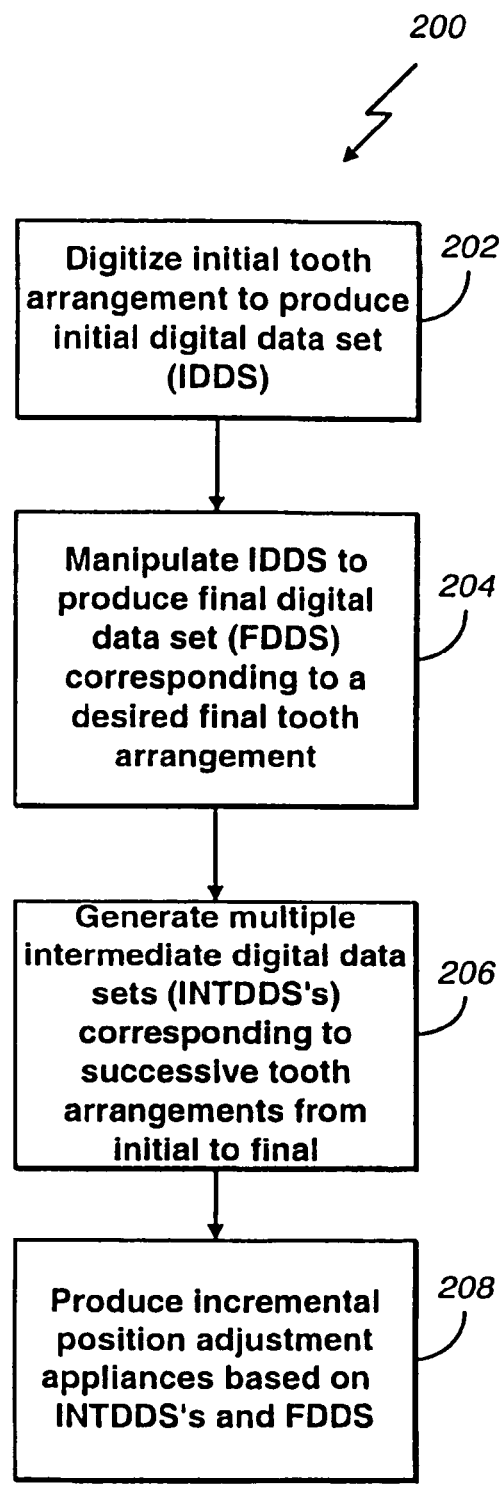
FIG. 3 is a block diagram illustrating a process for producing incremental position adjustment appliances.

FIG. 3 shows a process 200 for producing the incremental position adjustment appliances for subsequent use by a patient to reposition the patient's teeth. As a first step, an initial digital data set representing an initial tooth arrangement is obtained (202). The initial data set may be obtained in a variety of ways. For example, the patient's teeth may be scanned or imaged using X-rays, three dimensional X-rays, computer-aided tomographic images or data sets, or magnetic resonance images, among others. The teeth data may be generated by a destructive scanner, as described in the incorporated-by-reference U.S. application Ser. No. 09/169,034, filed Oct. 8, 1998. The initial data set is then manipulated using a computer having a suitable graphical user interface (GUI) and software appropriate for viewing and modifying the images (204). More specific aspects of this process will be described in detail below. Individual tooth and other components may be segmented or isolated in the model to permit their individual repositioning or removal from the digital model.

After segmenting or isolating the components, the teeth are moved based on rules and algorithms programmed into the computer. In this step, an attraction model between selected points on adjacent teeth determines each stage of tooth movement. This step is iterated until an acceptable result is achieved. In one embodiment, the system stops the movement when the relative positions of the teeth satisfy a predetermined target.

In step 206, multiple intermediate digital data sets (INTDDS') are formed and the positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement, which is customized to the patient's teeth, as discussed below. After applying the ideal model to the computer representation, the position of the teeth can be optimized to fit the ideal model. One or more arch forms may specify the ideal model, or may be specified using various features associated with the teeth.

During this process, the teeth models may be rotated until their roots are in the proper vertical position, for example. Next, the teeth models may be rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together can be visualized using a collision detection process to highlight the contacting points of the teeth.

Once the teeth arrangements are determined, a series of appliances that move the teeth in a specified sequence are generated (208).

As part of the generation of the initial digital data set representing an initial tooth arrangement of step 202, a bite-setting operation is performed on the upper and lower jaws. FIG. 4 shows one embodiment (300) of an Automated Bite Setting process. First, the system scans the lower arch. This can be done using a destructive scanner or a non-destructive scanner such as a white light scanner (302). Then, the upper arch is scanned, using the destructive Scanner or white light scanner (304). The upper and lower arches are wax-scanned in their bite position using white light scanner (306). Then the upper and lower arch scans are split apart (308). Finally, the bite is registered (310).

FIG. 5 describes the Wax Scan process (306) listed in FIG. 4. In one embodiment, a wax bite is placed between the upper and lower arches (322). The upper and lower arches are aligned, based on the wax bite, to indicate their normal bite position (324). Then the wax bite is removed (326). Finally, a buccal-view scan of the upper and lower arches is performed using the normal bite position without wax bite (328).

Figure 6:
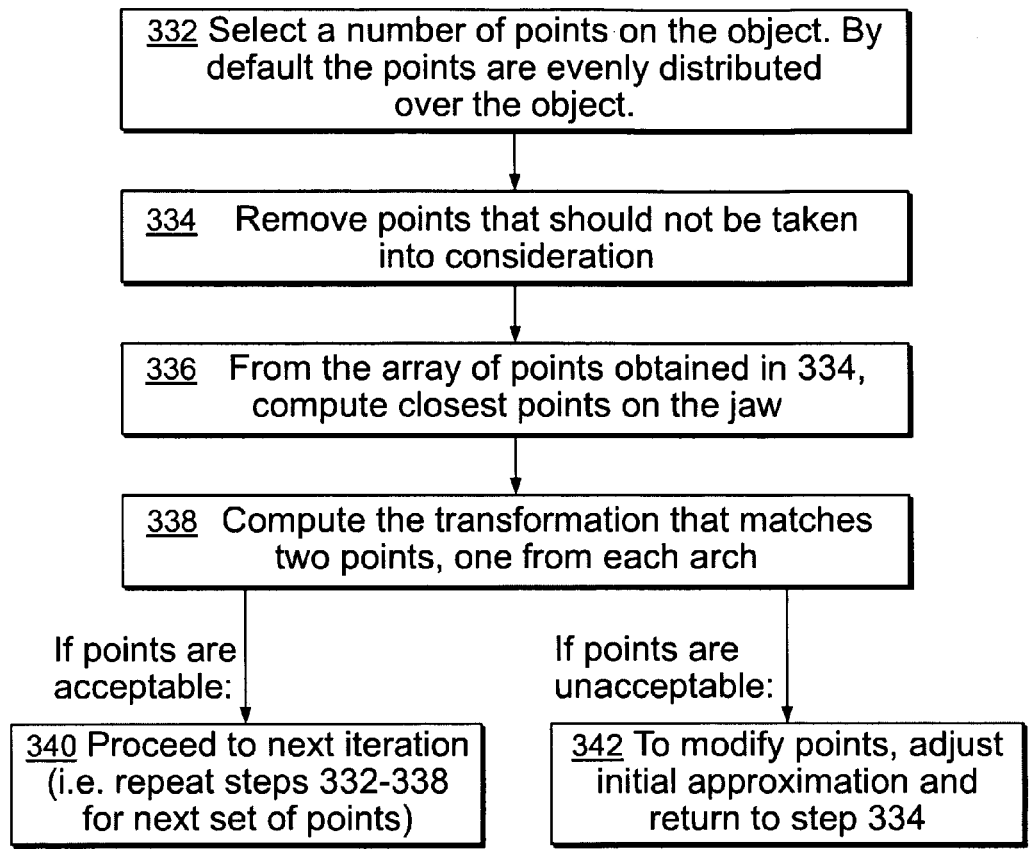

Referring now to FIG. 6, the process for generating the bite registration is described. This process is called geometry matching. The geometry matching iteration is the meshing of the three geometries involved in Bite Registration: the upper arch, the lower arch, and either the upper or lower arch in the normal bite position. In one implementation, the geometry matching iteration includes the following steps: first, select a number of points on the object (332). By default the points are evenly distributed over the object. Any other points should not be taken into consideration and are removed (334). In one implementation, if two non-identical surfaces are being matched, certain points should not be included. For example, two surfaces can have a common area that should be used for matching as well as undesirable or noisy data. To remove noisy data, the points may be filtered by analysis of the distance distribution. Only points that do not deviate from the average than +- dispersion are included in matching. It removes points that are far away compared with average, so the probability that matching would not converge is reduced. (It is likely that these points do not represent the area to be matched.) From the array of points obtained in 332, the closest points on the jaws are computed (336). Finally, the process computes the transformation that matches two points on the arches (338). It computes rigid transformation that minimizes the sum of squared distances between corresponding points. If the result is acceptable, proceed or go to the next iteration (340). If results need to be modified, adjust the initial approximation and return to 334 in operation 342.

Since the process is statistical (it requires many random iterations to compute the result) there is a small possibility that results may not fall within in the acceptable range. In this case the process is run again, or some random transformation may be added. Alternatively, the process may be stopped if the iterations exceed a predetermined threshold.

Figure 7:
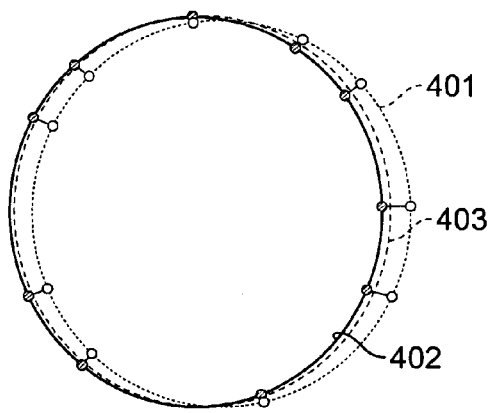
FIG. 7 illustrates the geometry matching process using circles.

FIG. 7 is a diagram illustrating the geometry matching process using three circles. Circle 401 is matched against circle 402, which represents the two non-identical surfaces being matched. Following the process described in FIG. 6, a number of points are selected on circle 401. Then each point is matched up with the closest point that can be found on circle 402. This process is called matching the two point sets. After the geometry matching transformation is complete, circle 401 is moved to its new position, indicated by circle 403.

FIGS. 8 through 11 are computer graphic images of an upper and lower jaw as it undergoes the bite registration process. FIG. 8 is a screenshot of the initial bite scan. FIG. 9 shows the first approximation once the initial orientation with the normal bite is guessed. FIG. 10 shows the separated bites for the lower and upper jaws. FIG. 11 shows the final result of the matching process.

FIG. 12 depicts the process of utilizing physical simulation and collision detection to determine proper occlusion. Assuming that the jaws are nearly in the correct and optimal position, the ideal process simulates the way a patient closes his mouth. Implementation of the algorithm is as follows: first, the upper jaw is moved closer to the lower, for example, in the Z-axis direction (350). It is to be noted that the approach is not limited to the upper jaw: one can apply the application to the lower jaw or to both jaws at the same time. The collisions are computed (352). The collision areas are minimized using an appropriate algorithm (354). There are numerous possible implementations of such an algorithm. FIGS. 13 and 14 describe potential implementations of minimizing collision areas.

FIG. 13 shows one such collision minimization implementation. This implementation attempts to rotate or shift the upper jaw in all 5 degrees of freedom, with the Z direction excluded (360). Then the position is selected where the collision area or any other appropriate measure of collision (for example, collision volume) is minimal (362). Next, the collision areas are minimized using an appropriate algorithm (364).

FIG. 14 describes the second implementation of the algorithm. This implementation is a 'brute force' approach, which can be more computationally lengthy, but is a cost effective approach. The direction to move the jaw is selected by using dental knowledge of the collision areas between the jaws (370). For example, each collision area exerts a force on the upper jaw. The direction of the force may be the average normal for the faces in the collision area. By using simple mechanical laws (Arnold, 1973, 1989), one creates a system of differential equations, and then solves them in a number of iterative steps (372). The process stops when it is impossible to move the upper jaw further down without introducing acceptable (i.e. smaller than a user-specified value) collision areas that cannot be achieved through translation and rotation (374). Thus, using one of these two methods, proper occlusion is achieved.

In both algorithms, the user can control the limit of movement in all 5 degrees of freedom; this ensures that the algorithm does not converge to an undesirable local minimum. Both algorithms can be used to finding multiple paths to the best occlusion, by analyzing the paths; both algorithms provide a simulation of the actual teeth grinding with each other.

Exemplary pseudo-code to perform a bite setting with two jaw models is as follows:

Scan Lower Arch using the Destructive Scanner or White Light Scanner.
Scan Upper Arch using the Destructive Scanner or White Light Scanner.
Wax Scan the Upper and Lower Arches in their bite position using White Light Scanner:
Place wax bite between upper and lower arches.
Align the upper and lower arches based on wax bite to indicate their normal bite position.
Remove wax bite.
Perform buccal scan of upper & lower arch in normal bite position without wax bite.
Split apart the upper and lower arch scans.
Register the bite using Geometry Matching.
Select a number of points on the object. By default the points are evenly distributed over the object.
Remove points that should not be taken into consideration.
For the array of points obtained, compute closest points on the jaw.
Compute the transformation that matches two points, one from each arch.
If points are acceptable, proceed to next iteration (i.e. repeat all steps listed above for the next set of points).
If points are unacceptable, modify the points by adjusting the initial approximation, remove the points that should not be taken into consideration, compute the closest points on the jaw, and then compute the transformation that matches two points, one from each jaw.

Exemplary pseudo-code to create a proper occlusion between the two jaw models is as follows:

Move the upper jaw closer to the lower, for example, in the Z axis direction.
Compute collisions.
Minimize the collision areas using an appropriate algorithm. Two potential implementations can be done:

Implementation 1:
Attempt to rotate or shift the upper jaw in all 5 degrees of freedom, with the Z direction excluded.
Select the position in which the collision area or any other appropriate measure (for example, collision volume) is minimal.
Minimize the collision areas using an appropriate algorithm.

Implementation 2:
Select the direction to move the jaw by using dental knowledge of the collision areas between the jaws.
Using mechanical laws, one creates a system of differential equations, which are used to reduce the collision area.
The process stops when it is impossible to move the upper jaw further down without introducing acceptable collision areas that cannot be achieved through translation and rotation.

Figure 15:
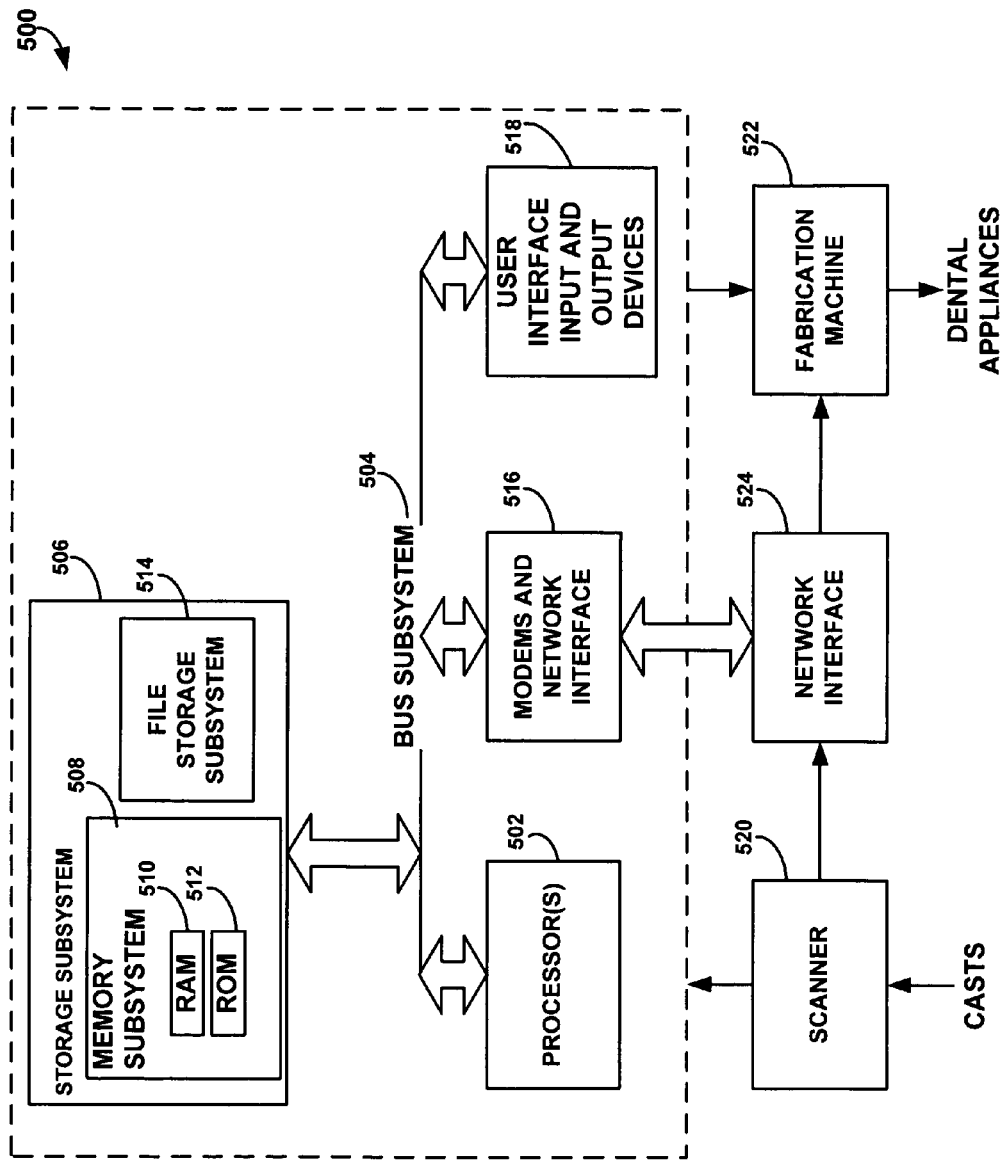
FIG. 15 is a block diagram illustrating a system for generating appliances in accordance with the present invention.

FIG. 15 is a simplified block diagram of a data processing system 500. Data processing system 500 typically includes at least one processor 502 that communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe. The user interface input devices typically include a keyboard and may further include a pointing device and a scanner. The pointing device may be an indirect pointing device such as a mouse, trackball, touch pad, or graphics tablet, or a direct pointing device such as a touch screen incorporated into the display. Other types of user interface input devices, such as voice recognition systems, may be used. User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514. Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system). File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web. In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations. Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system. Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524. Fabrication machine 522 fabricates dental appliances based on intermediate and final data set information received from data processing system 500. In a distributed environment, fabrication machine 522 may be located at a remote location and receive data set information from data processing system 500 over network interface 524.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription. Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner. Further, while the invention has been shown and described with reference to an embodiment thereof, those skilled in the art will understand that the above and other changes in form and detail may be made without departing from the spirit and scope of the following claims.

What is claimed is:

1. A method to bite set a dental model, comprising:
    scanning upper and lower arches of the dental model;
    scanning the upper and lower arches in their bite position; and
    aligning the upper and lower arches to bite set the dental model, wherein the bite setting uses geometry matching, further comprising:
        selecting a predetermined number of points on the jaw model;
        removing noisy points;
        computing closest points on the jaw component; and
        computing a transformation that matches two points, one from each jaw model.

2. The method of claim 1, wherein the scanning uses a destructive scanner.

3. The method of claim 1, wherein the scanning uses a non-destructive scanner.

4. The method of claim 1, wherein the scanning uses a white light scanner.

5. The method of claim 1, wherein the scanning of the arches in their bite position further comprises:
    placing a wax bite between the upper and lower arches;
    positioning the upper and lower arches based on the wax bite to a bite position;
    removing wax bite; and
    performing a buccal scan of the upper and lower arches in the bite position without wax bite.

6. The method of claim 1, further comprising analyzing the next point if the current point satisfies a predetermined constraint.

7. The method of claim 6, wherein if the current point fails the predetermined constraint, further comprising:
    modifying the point by adjusting an initial approximation;
    removing the noisy points;
    computing closest points on the jaw models, and
    computing the transformation that matches two points, one from each jaw.

8. The method of claim 1, wherein the points are evenly distributed over the jaw models.

9. The method of claim 1, further comprising creating an occlusion between the two jaws.

10. The method of claim 9, wherein the collision criteria includes a collision area or a collision volume.

11. The method of claim 9, wherein the minimizing collision criteria further comprises:
    moving the upper jaw in a plurality of degrees of freedom and excluding a Z direction;
    selecting a position in which the collision criteria is minimal.

12. The method of claim 9, wherein the minimizing collision criteria further comprises:
    selecting a direction to move the jaw by using dental knowledge of the collision areas between the jaws; and
    iteratively reducing the collision area using mechanical physics.

13. The method of claim 12, wherein the iteratively moving the jaw avoids introducing collision areas that cannot be achieved through translation and rotation.

14. The method of claim 1, further comprising:
moving the upper jaw closer to the lower jaw;
computing collisions between the jaw models; and
minimizing one or more collision criteria.

15. The method of claim 14, wherein moving the jaws comprises moving in a Z axis direction.

16. A dental modeling system, comprising:
means for scanning upper and lower arches of the dental model:
means for scanning the upper and lower arches in their bite position; and
means for aligning the upper and lower arches to bite set the dental model, wherein the bite setting uses geometry matching, further comprising:
means for selecting a predetermined number of points on the jaw model;
means for removing noisy points;
means for computing closest points on the jaw component; and
means for computing a transformation that matches two points, one from each jaw model.

\* \* \* \* \*